United States Patent [19]

Valsecchi et al.

[11] Patent Number: 5,744,497
[45] Date of Patent: Apr. 28, 1998

[54] TRINUCLEAR CATIONIC PLATINUM COMPLEXES HAVING ANTITUMOR ACTIVITY AND PHARMACEUTICAL COMPOSITIONS CONTAINING THEM

[75] Inventors: Mariella Valsecchi; Marco Conti; Luisa Del Greco; Carlo Bugatti; Ernesto Menta; Ferdinando Giuliani; Carla Manzotti; Silvano Spinelli, all of Monza, Italy; Nicholas Farrell, Richmond, Va.

[73] Assignee: Boehringer Mannheim Italia, S.p.A., Milan, Italy

[21] Appl. No.: 714,083

[22] PCT Filed: Mar. 22, 1995

[86] PCT No.: PCT/EP95/01074

§ 371 Date: Sep. 27, 1996

§ 102(e) Date: Sep. 27, 1996

[87] PCT Pub. No.: WO95/26968

PCT Pub. Date: Oct. 12, 1995

[30] Foreign Application Priority Data

Mar. 31, 1994 [IT] Italy ................... MI94A0610

[51] Int. Cl.$^6$ ...................... C07F 15/00; A61K 31/28
[52] U.S. Cl. .............................. 514/492; 556/137
[58] Field of Search ..................... 556/137; 514/492

[56] References Cited

U.S. PATENT DOCUMENTS 5,049,686 9/1991 Hoeschele ........................ 556/137
5,380,897 1/1995 Hoeschele et al. ................. 556/137

FOREIGN PATENT DOCUMENTS 0 503 830A1 3/1991 European Pat. Off. .

OTHER PUBLICATIONS

Chemical Abstracts, vol. 119, No. 21, 22 Nov. 1993.
Biochemistry, vol. 29, No. 41, 1990, pp. 9522–9531.
Chemical Abstracts, vol. 118, No. 24, Jun. 14, 1993.
WO,A, 91 03482, Published Mar. 21, 1991.

*Primary Examiner*—Porfirio Nazario-Gonzalez
*Attorney, Agent, or Firm*—Nikaido Marmelstein Murray & Oram, LLP

[57] ABSTRACT

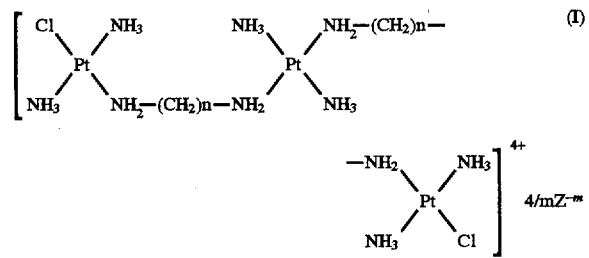

Compounds of general formula (I) wherein: n is an integer from 2 to 7 included; $Z^{-m}$ is an anion selected from chloride, bromide, iodide, nitrate, sulfate; m is the integer 1 or 2. Said compounds have antitumour activity.

19 Claims, No Drawings

TRINUCLEAR CATIONIC PLATINUM COMPLEXES HAVING ANTITUMOR ACTIVITY AND PHARMACEUTICAL COMPOSITIONS CONTAINING THEM

CROSS-REFERENCE TO RELATED APPLICATION

This application was filed under 35 U.S.C. § 371 as a request for U.S. examination of International application No. PCT/EP95/01074 filed Mar. 22, 1995.

The present invention relates to platinum-complexes having anti-tumour activity, processes for the preparation thereof and pharmaceutical compositions ontaining them.

TEXHNOLOGICAL BACKGROUND

The use of platinum complexes such as cisplatin and carboplatin in cancer chemotherapy is well stablished in the art. A number of platinum complexes, such as cis-platin, are used to treat testicular, ovarian, head and neck, and small-cell lung carcinomas. However, treatment with cisplatin may result in severe nephrotoxicity. A further clinical disadvantage is the problem of acquired drug resistance resulting in the tumor becoming refractory to treatment by the agent.

It is generally believed that platinum complexes such as cisplatin manifest their biological activity through covalent interaction with DNA. In particular, cisplatin induces the formation of a range of adducts on DNA including monodentate adducts, bidentate adducts, such GG or AG, and GNG intrastrand crosslinks [Reedijk et al., *Structure and Bonding*, (1987) 67, 53–89]. To a lesser extent, cisplatin also results in interstrand GG crosslinks and DNA-protein crosslinks [Rahmouni et al., *Biochemistry*, (1987) 26, 7229–7234]. These DNA lesions result in conformational changes which are reflected in bending and local unwinding of the DNA. These DNA lesions have been reported to inhibit the activity of various DNA polymerases [Vallan et al., *Nucl. Acids Res.*, (1988) 16, 4407–4418; Pinto et al., *Proc. Natl. Acad. Sci.*, (1985) 82, 4616–4619; and Gralla et al., *Cancer Res.*, (1987) 47, 5092–5096]. The interstrand crosslink between two neighboring guanine bases has also been shown to inhibit RNA polymerase function. [Lemaire et al., *Proc. Natl. Acad. Sci.*, (1991) 88, 1982–19851. Accordingly, the cytotoxic effects of cisplatin are most likely attributable to the combined effects of these DNA lesion, rather than the result of any one specific lesion event.

Mono(platinum) and bis(platinum) complexes respectively containing one or two platinum atoms are known in the art (U.S. Pat. Nos. 4,225,529, 4,250,189, 4,533,502, 4,565,884, 4,571,335 and 4,797,393). For example, mono (platinum) complexes include monomeric chloramine square-planar Pt(II) compounds which are four coordinate. The relative number of chloride and ammonia groups in such compounds may vary and these compounds may therefore be described by the general formula:

$$[PtCl_m(NH_3)_{4-m}]^{(2-m)+}$$

Thus, the structure of these compounds may vary from $[Pt(NH_3)_4]^{2+}$ where m=0 to $PtCl_4^{2-}$ where m=4. Since Cl is more substitution labile in comparison to ammonia, the complexes $[PtCl_2(NH_3)_2]$ and $[PtCl(NH_3)_3]Cl$ are considered bifunctional and monofunctional respectively, wherein the "bi" and "mono" prefixes refers to the number of leaving ligands. The charge of the complexes is obtained by considering that the Pt(II)cation has a formal charge of +2 and thus requires a negative charge of −2 for charge neutralization. For example, when m=0, neutralization is provided by the presence of two chloride anions outside the coordination sphere.

The formation of the bond between platinum and ammonia, which is a neutral ligand, may be described as electron-pair donation from $NH_3$ to the empty orbitals on the Pt(II) atom. Thus, no electron sharing between the Pt and $NH_3$ group takes place. Because of this absence of electron sharing, the number of neutral ligands does not affect the overall charge in the Pt coordination sphere. Thus $[Pt(NH_3)_4]^{2+}$ is formally a 2+ cation requiring non-coordinating anion or anions, or counter-ions, having a net negative charge of 2− for neutralization of the complex. For example, neutralization can be provided by two mononegatively charged anions (e.g., $NO_3^-$, $Cl^-$, $PF_6^-$, $BF_4^-$ and monocarboxylates having the general formula $RCOO^-$) or a single dinegatively charged anion (e.g., $SO_4^{2-}$, dicarboxylates having the general formula $(R(COO)_2]^{2-}$. Therefore, for the same principles, $[PtCl_2(NH_3)_2]$ is a neutral complex.

These considerations can be applied not only to ammonia, but to neutral ligands such as primary or secondary amines as well.

It is noted that anionic ligands such as $Cl^-$ may be either coordinately bound (i.e., forming a Pt—Cl bond) or may act as a counter-anion without any need for covalent bond formation. The exact form that anions such as $Cl^-$ are comprised in a given platinum complex depends both on theoretical considerations (kinetic vs. thermodynamic effects) and the actual synthetic procedures utilized to make the complex (e.g., the extent of reaction, acidity, concentration of the particular anion, such as the concentration of $Cl^-$ which is contained in the reaction mixture. These considerations are applicable to other anionic and neutral ligands as well.

The fact that the overall charge of monoplatinum complexes depends on the relative number of neutral and anionic ligands which are bound to the Pt(II) metal is equally applicable for polynuclear complexes (which contain more than one Pt(II) coordinate spheres), and for Pt(IV) containing complexes wherein the oxidation state of the platinum moiety is 4+. For example, dinuclear complexes where two equivalent Pt(II) coordination spheres are linked by a diamine bridging agent may be represented by the general formula

Thus, when m=2 and two bifunctional coordination spheres are present, the compound is neutral. In contrast, when m=1, only monofunctional coordination spheres are present and the platinum moiety has a formal charge of 2+ which must be counterbalanced by one or more counter-anions having a net charge of 2−.

Examples of trinuclear platinum complexes (also named tri-platinum complexes) were recently reported in literature [Yun Qu et al., *Inorg. Chem.*, 32, 2591–2593 (1993)]. Said compounds, in which the ligands have a cis configuration, are complexes neutral or bearing an overall charge of +2 and they can be represented by the following general formulae:

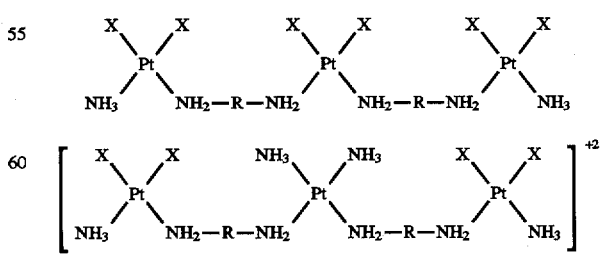

in which X means a labile ligand (such as a chlorine atom) and R means an alkylene chain. From what stated above, it is evident that, in the case of the complexes with an overall charge of +2, said charge is located on the central platinum atom, bearing four neutral ligands, whereas the two peripheral platinum atoms are formally neutral and, as defined above, bifunctional. Said complexes are described to be possible antitumour agents, but no experimental evidences are given.

DISCLOSURE OF THE INVENTION

The present invention relates to tri-platinum complexes in which the three platinum atoms are linked by diamine chains and in which the central platinum atom coordinates four neutral ligands, whereas the two peripheral platinum atoms both coordinate three neutral ligands and one ligand having charge −1.

Therefore, the compounds of the present invention are different from the compounds of the prior art in having an overall charge of +4 and in particular in having the central platinum atom with a formal charge of +2 and the two peripheral platinum atoms each with a formal charge of +1.

Moreover, as evidenced above, the two peripheral platinum atoms are monofunctional.

A further difference from the tri-platinum complexes described in the prior art is that in the compounds of the present invention the ligands are in trans configuration.

Particularly, the invention relates to triplatinum complexes of formula (I):

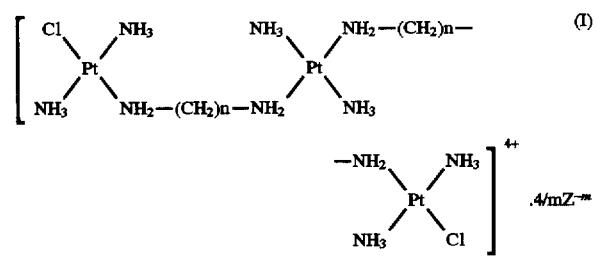

wherein n is an integer from 2 to 7 included;
$Z^{-m}$ is an anion selected from chloride, bromide, iodide, nitrate, sulfate (m=2);
m is the integer 1 or 2.

Preferred compounds of formula (I) are those in which n is the integer 6.

Particularly preferred compounds of formula (I) are those in which n is the integer 6, $Z^{-m}$ is a chloride or nitrate anion, and m is 1.

The present invention also relates to the processes for the preparation of the compounds of formula (I).

A method for the preparation of the compounds of formula (I) is that involving the synthesis of the intermediate (III) starting from trans-platinum, previously activated by substitution of a chlorine atom with dimethylformamide, by reaction with an amine of formula (II), as shown in the following scheme:

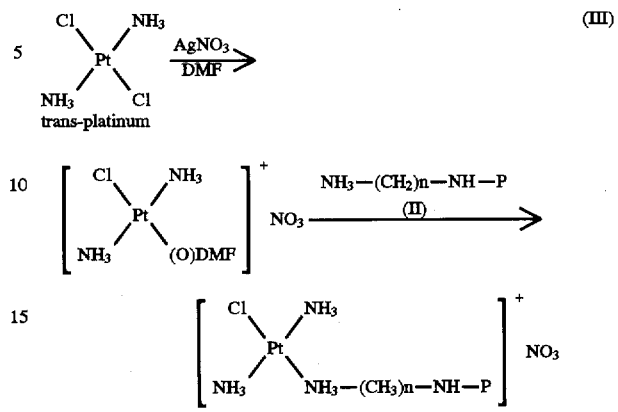

wherein P is a suitable conventional protecting group such as tert-butoxycarbonyl or p-methoxybenzyloxycarbonyl, n is as above defined.

The intermediate of formula (III) yields, after cleavage of the protecting group P, the intermediate of formula (IV):

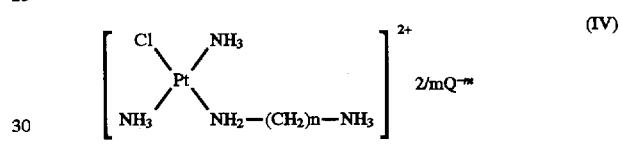

in which n is as defined above, $Q^{-m}$ is a counter-ion which depends on the conditions of cleavage of the group P. For example, if P is a tert-butoxycarbonyl group, $Q^{-m}$ can be a chloride or trifluoroacetate anion.

The intermediate (IV) is then transformed into the intermediate (V):

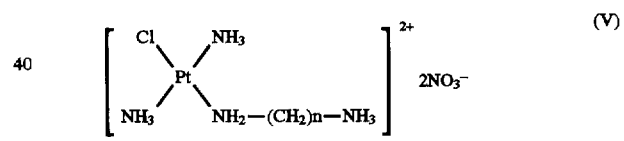

wherein n is as defined above, by means of an exchange reaction between the $Q^{-m}$ ion and the nitrate ion. Said exchange reaction, when $Q^{-m}$ is a chloride anion, can be carried out in the presence of silver nitrate and in solvents such as water or alcohols (methanol, ethanol).

The intermediate (V) is then reacted with half a mole of trans-platinum, previously activated by substitution of both the chlorine atoms with two molecules of dimethylformamide, to give the compounds of formula (I):

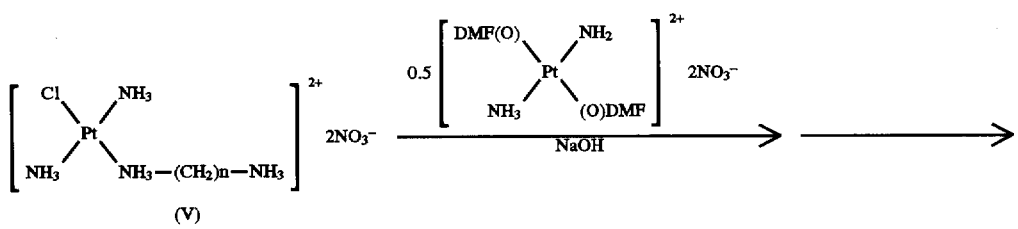

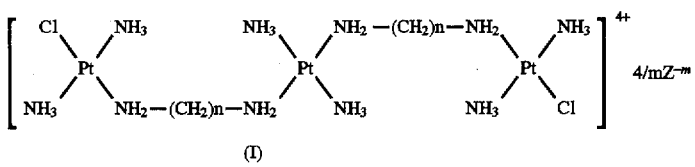

(I)

in which $Z^{-m}$ is a nitrate anion. Said compounds can then be transformed into the compounds of formula (I) in which $Z^{-m}$ is halide or sulfate by conventional exchange reactions, widely reported in literature, such as treatment with an alkali or alkaline-earth metal halide or sulfate. Alternatively, compounds of formula (I) in which $Z^{-m}$ is a sulfate anion can be obtained from the corresponding compounds of formula (I) with $Z^{-m}$=halide, by treatment with silver sulfate.

A preferred method for preparing compounds (I) with $Z^{-m}$=chloride from compounds (I) with $Z^{-m}$=nitrate is the reaction with a molar excess of hydrochloric acid at a temperature ranging from 0° C. to 50° C.

Another method for the preparation of the compounds of formula (I) consists in reacting first two moles of the amine of formula (II) with trans-platinum, previously activated by substitution of both the chlorine atoms with two molecules of dimethylformamide, to give the intermediate of formula (VI):

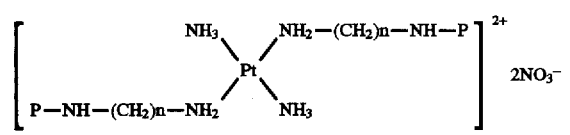
(VI)

wherein P has the meanings defined above. The cleavage of the groups P leads to the intermediate of formula (VII), wherein $Q^{-m}$ has the meanings defined above, which is subsequently transformed into the intermediate of formula (VIII):

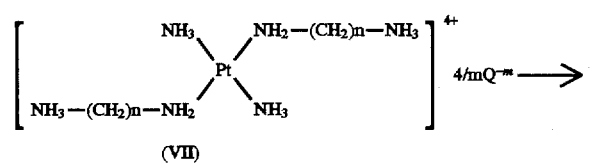
(VII)

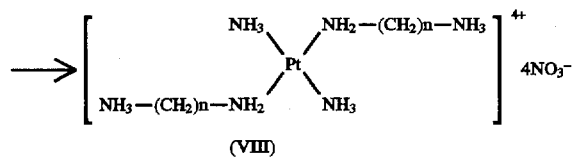
(VIII)

Said transformation is carried out by means of an exchange reaction between the $Q^{-m}$ ion and the nitrate ion. Said exchange reaction, when $Q^{-m}$ is a chloride anion, can be carried out in the presence of silver nitrate and in solvents such as water or alcohols (methanol, ethanol).

The intermediate (VIII) is then reacted with two moles of trans-platinum, previously activated by substitution of a chlorine atom with dimethylformamide, to give the compounds of formula (I):

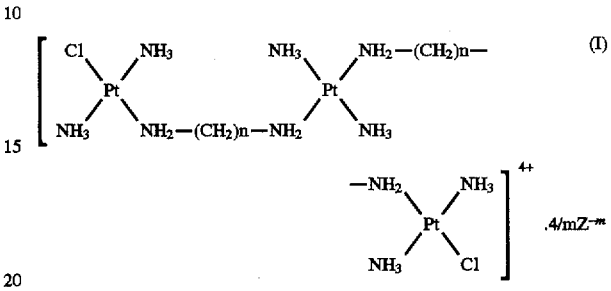
(I)

in which $Z^{-m}$ is a nitrate anion. Said compounds can then be transformed into the compounds of formula (I) in which $Z^{-m}$ is halide or sulfate by conventional exchange reactions widely reported in literature, such as treatment with an alkali or alkaline-earth metal halide or sulfate. Alternatively, compounds of formula (I) in which $Z^{-m}$ is a sulfate anion can be obtained from the corresponding compounds of formula (I) with $Z^{-m}$=halide by treatment with silver sulfate.

A preferred method for preparing compounds (I) with $Z^{-m}$=chloride from compounds (I) with $Z^{-m}$ nitrate is the reaction with a molar excess of hydrochloric acid at a temperature ranging from 0° C. to 50° C.

Possible methods for removing the groups P involve the treatment with inorganic (such as aqueous hydrochloric acid or in alcohol or ether solution) or organic acid (such as trifluoroacetic acid). When P is a tert-butoxycarbonyl group, preferred conditions for its cleavage are those which envisage the use of hydrogen chloride in alcoholic solution. In this case, as stated above, the counter-ion $Q^{-m}$ will be the chloride ion.

The compounds of the invention generally have a good solubility in water, in physiological and in water-miscible solvents.

The compounds of the invention not only have a marked antitumour activity, but also a low toxicity, therefore their therapeutical index is particularly favourable.

Moreover, the high water-solubility of the tri-platinum complexes of the present invention, makes the preparation of the parenteral and oral pharmaceutical forms easy.

The compounds of the invention were tested for their cytotoxic effect in vitro on various tumours cell lines, among which murine leukemia L-1210, human ovary carcinoma A2780 or the respective cis-platin resistant sub-lines L-1210/CDDP and A2780/CDDP. The test on the cell line A2780 is an established method for the evaluation of platinum complexes as antitumour agents. Moreover, the compounds of the invention were tested in an in vivo test in which L-1210 tumour cells are inoculated intraperitoneally in a mouse and the compound is administered intraperitoneally 24, 120 and 216 hours after inoculation of the tumour. The compounds of the invention evidenced a high antitumour effect in the above experimental models.

The compounds of formula (I), when administered to humans and animals bearing tumours which can be treated with platinum complexes, at doses ranging from 0.1 mg to 1.2 g per square meter of body area, are capable of inducing the regression of said tumours.

Therefore, another object of the present invention is the use of the compounds of formula (I) for the preparation of a medicament useful for the treatment of tumours.

The effective dosage of the compounds of the invention can be determined by expert clinicians according to conventional methods. The relationship between the dosages used for animals of various species and sizes and those for humans (on the basis of mg/m$^2$ body area) is described by Freirech, E. J. et al., *Quantitative Comparison of Toxicity of Anticancer Agents in Mouse, Rat, Hamster, Dog, Monkey and Man, Cancer Chemother. Rep.*, 50, N. 4, 219–244 (1966).

Usually, however, the patient will receive doses from 0.1 to 1200 mg/kg body weight of the complex, with a dosage regimen which will vary depending on various factors which are well known to the expert clinicians.

Sometimes it can prove advantageous to administer the platinum complexes of the present invention together with one or more agents which enhance the antitumour activity or relieve the undesirable side-effects of the platinum complex.

For example, the platinum complexes of the present invention can be administered together with reduced glutathione, as disclosed in GB 2174905 and U.S. Pat. No. 4,871,528.

Moreover, it can be advantageous to administer the platinum complexes of the present invention in combination with other platinum complexes having antitumour activity.

A pharmaceutical composition containing at least one compound of formula (I) in combination with a platinum complex having antitumour activity is a further object of the present invention.

The tumours in patients which can be treated with the platinum complexes of the present invention are those tumours known to be susceptible to the therapy with cis-platinum. The complexes of the present invention are also active against some cis-platinum resistant tumours.

More generally, the compounds of the invention can be used for the treatment of the same pathological forms for which cis-platinum is used. This includes the treatment of tumours, sensitization or enhancement of radiations [Douple et al., *Cisplatin Current Status and Developments*, Ed. A. W. Prestayk et al., Academic Press, 125 (1980); Douple et al., *Platinum Metals Res.*, 29, 118 (1985)] and the treatment of parasitic diseases such as African sleeping sickness [Farrell et al., *Biochem. Pharmacol.*, 33, 961 (1984)].

The treatment regimen can suitably be varied, as it is well known to the expert clinician, according to the type of tumour to treat and the conditions of the patient.

A further object of the present invention are pharmaceutical compositions containing a therapeutically effective amount of at least one compound of formula (I) in admixture with conventional carriers and excipients.

The compounds of the invention are preferably administered as sterile aqueous solutions, optionally containing sodium chloride in suitable concentration (0.1–0.9 mg/ml). The solutions are preferably administered by the intravenous or intra-arterial routes, even though other administration forms can be used in particular cases.

The pharmaceutical compositions for the parenteral administration comprise sterile saline solutions, as defined above, or sterile powders for the extemporary preparation of the solutions, as well as oily preparations for intramuscular or intraperitoneal administrations.

Other useful pharmaceutical compositions can be syrups or similar liquid forms, as well as solid forms such as tablets, capsules and the like.

The pharmaceutical compositions according to the present invention are prepared according to known methods, such as those reported in *Remington's Pharmaceutical Sciences Handbook*, XVII Ed., Mack Pub., N.Y., U.S.A..

The following examples further illustrate the invention.

PREPARATION 1

N-BOC hexanediamine is prepared starting from its hydrochloric salt, which is a commercial product.

2.1 g of N-BOC hexanediamine hydrochloride are dissolved in diethylether (20 ml) and treated under stirring with 16 ml of 1N aqueous solution of sodium hydroxide.

The organic phase is then washed with brine, dried over sodium sulfate and the solvent is evaporated off under reduced pressure to give N-BOC hexanediamine, free base, with a theorical yield.

EXAMPLE 1

Preparation of t-[PtCl(NH$_3$)$_2$H$_2$N-(CH$_2$)$_6$-NH-BOC]$^+$NO$_3^-$ 2 g of trans-platinum are dissolved in 133 ml of anhydrous dimethylformamide (DMF) and added with 1.13 g of silver nitrate in one portion. The reaction mixture is kept under stirring shielded from light for 18 hours. After that, the precipitated silver chloride is filtered off and the clear filtrate is cooled to –20° C. and added with a solution of N-BOC-1,6-hexanediamine (1.36 g) in 40 ml of anhydrous DMF. The addition lasts about 30 minutes. The solution is kept under stirring at –20° C. for 3 hours and for one hour at room temperature. Solvent is then evaporated under reduced pressure keeping the temperature of the solution not above 40° C. and the residue is taken up into 200 ml of ethyl ether, kept under stirring for 20 minutes, then filtered. The resulting solid is dissolved in 200 ml of methanol and kept under stirring for 15 hours to precipitate any traces of trans-platinum. The separated trans-platinum is filtered off and the solution is treated with active carbon (1 g), filtered again and finally the solvent is evaporated off under reduced pressure. The residue is purified by suspending it in acetone (100 ml) under stirring for 30 minutes. After filtration, 2.3 g of product are obtained.

Elementary analysis (calculated/found %): C 24.33/24.05; H 5.57/5.64; N 12.90/12.84; Cl 6.53/6.40; Pt 35.93/36.06.

$^{195}$Pt-NMR in DMF/d7-DMF: –2433 ppm.

EXAMPLE 2

Preparation of t-[PtCl(NH$_3$)$_2$H$_2$N-(CH$_2$)$_6$-NH$_3$]$^{2+}$ 2NO$_3^-$

A solution of 1.5 g of t-[PtCl(NH$_3$)$_2$H$_2$N-(CH$_2$)$_6$-NH-BOC]$^+$NO$_3^-$ in 150 ml of methanol is added with 21 ml of a 6.5M solution of hydrogen chloride in ethanol. The reaction mixture is kept under stirring for 24 hours at room temperature, then the solid is filtered, washed on the filter with methanol and ethyl ether and finally dried.

The resulting solid is dissolved in 180 ml of methanol and added with a solution of silver nitrate (0.825 g) in 45 ml of methanol. The reaction mixture is kept under stirring at room temperature for 30 minutes, the silver chloride is filtered off and the clear filtrate is evaporated to dryness. The residue is taken up with acetone, kept under stirring for 15 minutes, filtered and dried, to obtain 0.925 g of product.

Elementary analysis (calculated/found %): C 14.65/14.19; H 4.71/4.66; N 14.24/16.62; Cl 7.21/6.91; Pt 39.67/36.10.

$^{195}$Pt-NMR in DMF/d7-DMF: –2433 ppm.

EXAMPLE 3

Preparation of t,t,t-[PtCl(NH$_3$)$_2$H$_2$N-(CH$_2$)$_6$-NH$_2$-Pt(NH$_3$)$_2$H$_2$N-(CH$_2$)$_6$-NH$_2$PtCl(NH$_3$)$_2$]$^{4+}$4NO$_3^-$ 61 mg of trans-platinum are suspended in 2 ml of anhydrous dimethylformamide and added with 69.1 mg of silver nitrate. The reaction mixture is kept under stirring and at 65° C. for 6 hours, then it is cooled to room temperature and the silver chloride precipitate is filtered of. The filtrate is added with a solution of t-[PtCl(NH$_3$)$_2$H$_2$N-(CH$_2$)$_6$-NH$_3$]$^{2+}$2NO$_3^-$ (200 mg) in 2 ml of dimethylformamide and with 0.4 ml of 1N sodium hydroxide solution in methanol. The resulting reaction mixture is kept at room temperature overnight, then it is diluted with ethyl ether until separation of the solid which is filtered, washed with ethyl ether, then with acetone and finally dried, to obtain 220 mg of product.

Said product is suspended in DMF (5 ml) and kept under stirring for 10 minutes, then recovered by filtration and resuspended in acetone (10 ml), keeping it under stirring for a further 30 minutes. After filtration and drying, 150 mg of product are obtained.

Elementary analysis (calculated/found %): C 11.63/11.70; H 4.07/3.95; N 15.83/15.20; Cl 5.72/4.60; Pt 47.24/47.10.

$^{195}$Pt-NMR in NaCl 0.3% in water: −2416 ppm; −2667 ppm.

$^1$H-NMR (200 Mhz) in D$_2$O: 1.35 ppm (m, 8H); 1.68 ppm (m, 8H); 2.65 ppm (br m, 8H).

EXAMPLE 4

Preparation of t-[BOC-NH-(CH$_2$)$_6$-NH$_2$-Pt(NH$_3$)$_2$H$_2$N-(CH$_2$)$_6$-NH-BOC]$^{2+}$2NO$_3^-$ A suspension of 1.028 g of trans-platinum in 35 ml of anhydrous dimethylformamide is added with 1.16 g of silver nitrate. The reaction mixture is heated to 60° C., shielding from light, for 5 hours, then the silver chloride precipitate is filtered off. After that, a solution of N-BOC-1,6-hexanediamine (1.48 g) in 5 ml of dimethylformamide is added and the resulting reaction mixture is kept at room temperature overnight. By dilution with 300 ml of ethyl ether a white solid separates, which is filtered, redissolved in methanol and filtered through a 0.2 micron Millex filter to remove any traces of silver salts. The methanol solution is then diluted with ethyl ether. A white solid crystallizes which is filtered and dried, to obtain 1.94 g of product.

Elementary analysis (calculated/found %): C 33.63/33.44; H 6.93/7.00; N 14.26/14.30; Pt 24.83/25.06.

$^{195}$Pt-NMR in DMF/d7-DMF: −2687 ppm.

EXAMPLE 5

Preparation of t-[NH$_3$-(CH$_2$)$_6$-NH$_2$-Pt(NH$_3$)$_2$H$_2$N-(CH$_2$)$_6$-NH$_3$]$^{4+}$4Cl$^-$ 500 mg of t-[BOC-NH-(CH$_2$)$_6$-NH$_2$-Pt(NH$_3$)$_2$H$_2$N-(CH$_2$)$_6$-NH-BOC]$^{2+}$2NO$_3^-$ are dissolved in 50 ml of methanol and added with 5 ml of a 6.5M solution of hydrogen chloride in ethanol. The reaction mixture is kept under stirring at room temperature for 42 hours, then the solid is filtered and washed with ethyl ether, to obtain 340 mg of product.

Elementary analysis (calculated/found %): C 23.81/23.14; H 6.66/6.73; N 13.88/13.51; Cl 23.42/22.03; Pt 32.23/31.68.

$^{195}$Pt-NMR in water: −2674 ppm.

EXAMPLE 6

Preparation of t,t,t-[PtCl(NH$_3$)$_2$H$_2$N-(CH$_2$)$_6$-NH$_2$-Pt(NH$_3$)$_2$H$_2$N-(CH$_2$)$_6$-NH$_2$PtCl(NH$_3$)$_2$]$^{4+}$4NO$_3^-$ 200 mg of t-[NH$_3$-(CH$_2$)$_6$-NH$_2$-Pt(NH$_3$)$_2$H$_2$N-(CH$_2$)$_6$-NH$_3$]$^{4+}$4Cl$^-$ are dissolved in 10 ml of distilled water and treated with 224 mg of silver nitrate. The resulting suspension is kept at room temperature and under stirring for 10 minutes, then the silver chloride precipitate is removed by filtration. The filtrate is concentrated nearly to dryness, then diluted with acetone. A white solid separates which is filtered, washed with acetone and dried, to obtain 204 mg of t-[NH$_3$-(CH$_2$)$_6$-NH$_2$-Pt(NH$_3$)$_2$H$_2$N-(CH$_2$)$_6$-NH$_3$]$^{4+}$4NO$_3^-$.

A solution of 172 mg of trans-platinum in 21.5 ml of anhydrous dimethylformamide is treated with 98 mg of silver nitrate. The resulting suspension is kept under stirring at room temperature overnight, shielded from light, then the silver chloride precipitate is filtered off. A solution of 204 mg of t-[NH$_3$-(CH$_2$)$_6$-NH$_2$-Pt(NH$_3$)$_2$H$_2$N-(CH$_2$)$_6$-NH$_3$]$^{4+}$4NO$_3^-$ in 7 ml of dimethylformamide is treated with 0.57 ml of a 1N sodium hydroxide solution in methanol, then said solution is added at room temperature to the previous filtrate containing trans-platinum activated with dimethylformamide. After 6 hours the solution is filtered through a 0.2 micron Millex filter to remove any traces of silver salts, then the filtrate is diluted with ethyl ether. The precipitated solid is separated by filtration, to obtain 326 mg of product.

$^{195}$Pt-NMR in NaCl 0.3% in water: −2416 ppm; −2667 ppm.

$^1$H-NMR (200 Mhz) in D$_2$O: 1.35 ppm (m, 8H); 1.68 ppm (m, 8H); 2.65 ppm (br m, 8H).

EXAMPLE 7

Preparation of t,t,t-[PtCl(NH$_3$)$_2$H$_2$N-(CH$_2$)$_6$-NH$_2$-Pt(NH$_3$)$_2$H$_2$N-(CH$_2$)$_6$-NH$_2$PtCl(NH$_3$)$_2$]$^{4+}$4Cl$^-$ 326 mg of t,t,t-[PtCl(NH$_3$)$_2$H$_2$N-(CH$_2$)$_6$-NH$_2$-Pt(NH$_3$)$_2$H$_2$N-(CH$_2$)$_6$-NH$_2$PtCl(NH$_3$)$_2$]$^{4+}$4NO$_3^-$ are dissolved in a saline solution (0.9% sodium chloride), then the solution is filtered through a 0.2 micron Millex filter and concentrated until a white solid separates, which is filtered to yield 187 mg of product.

Elementary analysis (calculated/found %): C 12.73/12.60; H 4.45/4.45; N 12.37/12.85; Cl 18.78/14.77; Pt 51.68/48.33.

$^{195}$Pt-NMR in NaCl 0.3% in water: −2416 ppm; −2671 ppm.

$^1$H-NMR (200 Mhz) in D$_2$O: 1.40 ppm (m, 8H); 1.70 ppm (m, 8H); 2.70 ppm (br m, 8H).

EXAMPLE 8

Following the procedures described in Examples 1, 2 and 3, or alternatively the procedures described in Examples 4, 5 and 6, starting from the suitable monoprotected diamine, the following trans tri-platinum complexes are obtained:

[PtCl(NH$_3$)$_2$H$_2$N-(CH$_2$)$_5$-NH$_2$-Pt(NH$_3$)$_2$H$_2$N-(CH$_2$)$_5$-NH$_2$PtCl(NH$_3$)$_2$]$^{4+}$4NO$_3^-$;

[PtCl(NH$_3$)$_2$H$_2$N-(CH$_2$)$_4$-NH$_2$-Pt(NH$_3$)$_2$H$_2$N-(CH$_2$)$_4$-NH$_2$PtCl(NH$_3$)$_2$]$^{4+}$4NO$_3^-$;

[PtCl(NH$_3$)$_2$H$_2$N-(CH$_2$)$_3$-NH$_2$-Pt(NH$_3$)$_2$H$_2$N-(CH$_2$)$_3$-NH$_2$PtCl(NH$_3$)$_2$]$^{4+}$4NO$_3^-$;

[PtCl(NH$_3$)$_2$H$_2$N-(CH$_2$)$_2$-NH$_2$-Pt(NH$_3$)$_2$H$_2$N-(CH$_2$)$_2$-NH$_2$PtCl(NH$_3$)$_2$]$^{4+}$4NO$_3^-$;

[PtCl(NH$_3$)$_2$H$_2$N-(CH$_2$)$_7$-NH$_2$-Pt(NH$_3$)$_2$H$_2$N-(CH$_2$)$_7$-NH$_2$PtCl(NH$_3$)$_2$]$^{4+}$4NO$_3^-$.

$^{195}$Pt-NMR in NaCl 0.3% in water: −2422 ppm; −2670 ppm.

EXAMPLE 9

Following the procedure described in Example 7, starting from the trans tri-platinum complexes obtained according to Example 8, the following compounds are prepared:

[PtCl(NH$_3$)$_2$H$_2$N-(CH$_2$)$_5$-NH$_2$-Pt(NH$_3$)$_2$H$_2$N-(CH$_2$)$_5$-NH$_2$PtCl(NH$_3$)$_2$]$^{4+}$4Cl$^-$;

[PtCl(NH$_3$)$_2$H$_2$N-(CH$_2$)$_4$-NH$_2$-Pt(NH$_3$)$_2$H$_2$N-(CH$_2$)$_4$-NH$_2$PtCl(NH$_3$)$_2$]$^{4+}$4Cl$^-$;

[PtCl(NH$_3$)$_2$H$_2$N-(CH$_2$)$_3$-NH$_2$-Pt(NH$_3$)$_2$H$_2$N-(CH$_2$)$_3$-NH$_2$PtCl(NH$_3$)$_2$]$^{4+}$4Cl$^-$;

[PtCl(NH$_3$)$_2$H$_2$N-(CH$_2$)$_2$-NH$_2$-Pt(NH$_3$)$_2$H$_2$N-(CH$_2$)$_2$-NH$_2$PtCl(NH$_3$)$_2$]$^{4+}$4Cl$^-$;

[PtCl(NH$_3$)$_2$H$_2$N-(CH$_2$)$_7$-NH$_2$-Pt(NH$_3$)$_2$H$_2$N-(CH$_2$)$_7$-NH$_2$PtCl(NH$_3$)$_2$]$^{4+}$4Cl$^-$.

$^1$H-NMR (200 Mhz) in D$_2$O: 1.39 ppm (s, 12H); 1.68 ppm (br m, 8H); 2.67 ppm (br, m 8H).

EXAMPLE 10

Preparation of t,t,t-[PtCl(NH$_3$)$_2$H$_2$N-(CH$_2$)$_6$-NH$_2$-Pt(NH$_3$)$_2$H$_2$N-(CH$_2$)$_6$-NH$_2$-PtCl(NH$_3$)$_2$]$^{4+}$4Cl$^-$ A suspension of t,t,t-[PtCl(NH$_3$)$_2$H$_2$N-(CH$_2$)$_6$-NH$_2$-Pt(NH$_3$)$_2$H$_2$N-(CH$_2$)$_6$-NH$_2$-PtCl(NH$_3$)$_2$]$^{4+}$4NO$_3$ (1.3 g) in 0.1N aqueous hydrochloric acid (65 ml) was prepared under nitrogen atmosphere and then solubilized at 54° C. After 1 hour at this temperature the solution was cooled at 20° C. and filtered on a fiberglass filter to remove mechanical impurities: to the clear solution 7.8 ml of 4N acquous hydrochloric acid was added and in a few minutes the precipitation started. The suspension was stirred at 20° C. for 30 minutes, then for additional 30 minutes at 10° C. The precipitate was then filtered on a Buckner funnel and washed with 0.4N aqueous hydrochloric acid (0.5 ml) and acetone. The white collected solid was dried overnight under vacuum at 40° C. to yield 1.03 g of product.

Elementary analysis (calculated/found %)×2 H$_2$O: C 12.33/12.34; H 4.65/4.73; N 11.98/12.05; Cl 18.21/17.55; Pt 50.07/49.97.

We claim:

1. A compound of formula (I)

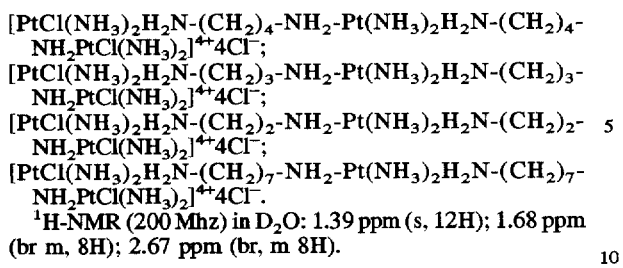
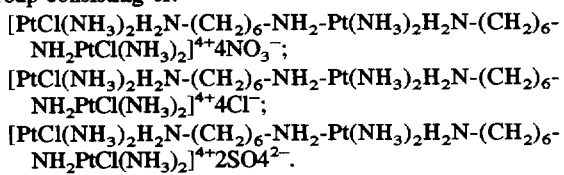

wherein:

n is an integer from 2 to 7 included;

Z$^{-m}$ is an anion selected from chloride, bromide, iodide, nitrate, sulfate;

m is the integer 1 or 2.

2. A compound according to claim 1, wherein n is the integer 6.

3. A compound according to claim 1, wherein Z is selected from chloride or nitrate and m is 1.

4. A compound according to claim 1, selected from the group consisting of:

[PtCl(NH$_3$)$_2$H$_2$N-(CH$_2$)$_6$-NH$_2$-Pt(NH$_3$)$_2$H$_2$N-(CH$_2$)$_6$-NH$_2$PtCl(NH$_3$)$_2$]$^{4+}$4NO$_3^-$;

[PtCl(NH$_3$)$_2$H$_2$N-(CH$_2$)$_6$-NH$_2$-Pt(NH$_3$)$_2$H$_2$N-(CH$_2$)$_6$-NH$_2$PtCl(NH$_3$)$_2$]$^{4+}$4Cl$^-$;

[PtCl(NH$_3$)$_2$H$_2$N-(CH$_2$)$_6$-NH$_2$-Pt(NH$_3$)$_2$H$_2$N-(CH$_2$)$_6$-NH$_2$PtCl(NH$_3$)$_2$]$^{4+}$2SO$_4^{2-}$.

5. A process for the preparation of a compound recited in claim 1, which comprises the following steps:

a) activation of trans-platinum by means of substitution of a chlorine atom with dimethylformamide in the presence of silver nitrate;

b) reaction of the activated intermediate with a diamine of formula (II)

H$_2$N—(CH$_2$)$_n$NH—P     (II)

wherein n is an integer from 2 to 7 included, P is a suitable conventional protecting group, to give, after cleavage of said protecting group P, the intermediate of formula (IV)

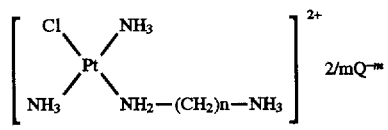

wherein n is as defined above, m is the integer 1 or 2 and Q$^{-m}$ is a counter-ion deriving from the conditions for the cleavage of the group P;

c) exchange reaction between the Q$^{-m}$ anion and the NO$_3^-$ anion in a solvent such as water or alcohol, to give the intermediate of formula (V)

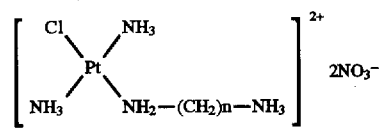

wherein n is as defined above;

d) reaction of the intermediate of formula (V) with trans-platinum, previously activated by substitution of two chlorine atoms with two molecules of dimethylformamide in the presence of silver nitrate, in a 1:0.5 mole ratio, to give a compound of formula (I) wherein n is as defined above, m is 1 and Z$^{-m}$ is the anion nitrate; and, if desired e) exchange reaction of said nitrate anion and another Z$^{-m}$ anion, wherein Z$^{-m}$ is as defined above.

6. A process according to claim 5, in which said group P is selected from tert-butoxycarbonyl and p-methoxybenzyloxycarbonyl.

7. A process according to claim 5, in which said group P is tert-butoxycarbonyl and the cleavage of said group is carried out with hydrochloric acid.

8. A process according to claim 5, wherein in step e) said anion nitrate is first exchanged with the Z$^{-m}$ chloride anion, then the chloride anion is exchanged with the sulfate anion, in which process the exchange between said chloride and said sulfate takes place by treatment with silver sulfate.

9. A process according to claim 5, wherein in step e) said anion nitrate is exchanged with the chloride anion by means of the reaction with aqueous hydrochloric acid in a molar excess at a temperature ranging from 0° C. to 50° C.

10. A process for the preparation of a compound recited in claim 1, which comprises the following steps:

a) reaction of an amine of formula (II)

H$_2$N—(CH$_2$)$_n$—NH—P     (II)

wherein n is an integer from 2 to 7 included, and P is a suitable conventional protecting group, with trans-platinum, previously activated by substitution of two chlorine atoms with two molecules of dimethylformamide in the presence of silver nitrate, in a 2:1 molar ratio, to give the intermediate of formula (VI)

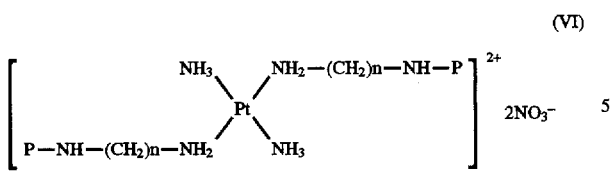

(VI)

wherein n and P are as defined above;

b) cleavage of the protecting group P to give the intermediate of formula (VII)

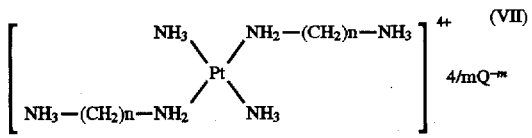

wherein n is as defined above and $Q^{-m}$ is an anion deriving from the cleavage reaction;

c) exchange reaction between the $Q^{-m}$ anion and the $NO_3^{31}$ anion, to give the corresponding nitrate of formula (VIII)

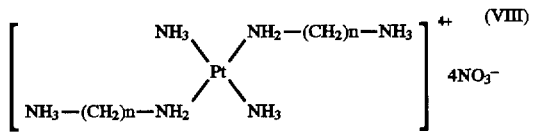

d) reaction of the intermediate of formula (VIII) with trans-platinum, previously activated by substitution of a chlorine atom with a molecule of dimethylformamide in the presence of silver nitrate, in a 1:2 molar ratio, to give a compound of formula (I)

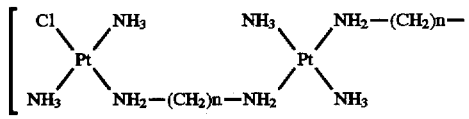

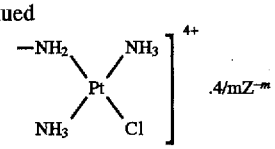

wherein n is as defined above, m is 1 and $Z^{-m}$ is the nitrate anion; and, if desired e) exchange reaction between said nitrate anion and another $Z^{-m}$ anion, wherein $Z^{-m}$ is as defined above.

11. A process according to claim 10, in which said group P is selected from tert-butoxycarbonyl and p-methoxybenzyloxycarbonyl.

12. A process according to claim 10, in which said group P is tert-butoxycarbonyl and the cleavage of said group is carried out with hydrochloric acid.

13. A process according to claim 10, wherein in step e) said nitrate anion is first exchanged with the $Z^{-m}$ chloride anion, then the chloride anion is exchanged with the sulfate anion, in which process the exchange between said chloride and said sulfate takes place by treatment with silver sulfate.

14. A process according to claim 10, wherein in step e) said anion nitrate is exchanged with the chloride anion by means of the reaction with aqueous hydrochloric acid in a molar excess at a temperature ranging from 0° C. to 50° C.

15. A method of treating a tumor in a patient in need of such treatment, comprising administering to said patient a tumor treatment effective amount of a compound as recited in claim 1.

16. A pharmaceutical composition comprising a therapeutically effective amount of at least one compound of claim 1 as the active ingredient, in admixture with at least one carrier or excipient.

17. A composition according to claim 16, in which said effective amount is so as to administer doses from 0.1 to 1200 mg/kg body weight of active ingredient active.

18. A composition according to claim 16 for parenteral administration.

19. Pharmaceutical composition according to claim 16, additionally containing a platinum complex having antitumour activity.

* * * * *